US012630800B2

(12) United States Patent
Alrokayan et al.

(10) Patent No.: US 12,630,800 B2
(45) Date of Patent: May 19, 2026

(54) SELF-ASSEMBLED COPOLYMERIC 3D NANOWIRE SCAFFOLD FOR CELL GROWTH AND PROLIFERATION, AND A METHOD FOR PRODUCING THEREOF

(71) Applicant: King Saud University, Riyadh (SA)

(72) Inventors: Salman Alrokayan, Riyadh (SA); Fouzi Mouffouk, Safat (KW); Haseeb Ahmad Khan, Riyadh (SA); Tajamul Hussain, Riyadh (SA); Salman Alamery, Riyadh (SA); Khalid M. Abu-Salah, Riyadh (SA)

(73) Assignee: King Saud University, Riyadh (SA)

(*) Notice: Subject to any disclaimer, the term of this patent is extended or adjusted under 35 U.S.C. 154(b) by 749 days.

(21) Appl. No.: 18/091,640

(22) Filed: Dec. 30, 2022

(65) Prior Publication Data

US 2023/0146437 A1 May 11, 2023

(51) Int. Cl.
*C12N 5/0735* (2010.01)
*C12M 1/12* (2006.01)

(52) U.S. Cl.
CPC .......... *C12N 5/0606* (2013.01); *C12M 25/14* (2013.01); *C12N 2513/00* (2013.01); *C12N 2533/40* (2013.01); *C12N 2533/52* (2013.01)

(58) Field of Classification Search
CPC .............. C12N 5/0606; C12N 2513/00; C12N 2533/40
See application file for complete search history.

(56) References Cited

U.S. PATENT DOCUMENTS

2008/0247987 A1* 10/2008 Liggins ................ A61K 9/0014 424/78.17

OTHER PUBLICATIONS

Li et al Biological response of chondrocytes cultured in three dimensional nanofibrous poly(-caprolactone) scaffolds, J Biomed Mater Res A 2003; 67: 1105-1114, published on Nov. 2003.*

* cited by examiner

*Primary Examiner* — Gregory Listvoyb
(74) *Attorney, Agent, or Firm* — Kilpatrick Townsend & Stockton LLP

(57) ABSTRACT

The present disclosure pertains to a 3D scaffold for cell growth and proliferation. In particular, the present disclosure provides a method of producing an artificial 3D scaffold to support stem cell growth and later their differentiation, by converting biodegradable amphiphilic copolymers (star polymer) into nanowire scaffolds, through a molecular self-assembly process. The invention also relates to the use of said scaffold for cell culture and/or transplantation.

8 Claims, 4 Drawing Sheets

SELF-ASSEMBLED COPOLYMERIC 3D NANOWIRE SCAFFOLD FOR CELL GROWTH AND PROLIFERATION, AND A METHOD FOR PRODUCING THEREOF

FIELD OF THE INVENTION

The present disclosure pertains to a 3D scaffold for cell growth and proliferation. In particular, the present disclosure provides a method of producing an artificial 3D scaffold to support stem cell growth and later their differentiation, by converting biodegradable amphiphilic copolymers (star polymer) into nanowire scaffolds, through a molecular self-assembly process. The invention also relates to the use of said scaffold for cell culture and/or transplantation.

BACKGROUND OF THE INVENTION

The background description includes information that may be useful in understanding the present invention. It is not an admission that any of the information provided herein is prior art or relevant to the present invention, or that any publication specifically or implicitly referenced is prior art.

Polymeric nanofibers represent an exciting new class of materials that has drawn substantial attention recently, particularly in the field of stem cell and tissue engineering. Such emphasis can be interpreted by the ability of these materials to mimic the arrangement of fibers and fibrils of the extracellular matrix (ECM), making them suitable for a wide range of medical applications in particular stem cell-based tissue engineering and medical textile materials. Increasingly, researchers believe that stem cell technology has the potential to drastically change our approach concerning disease treatment. Unfortunately, stem cells are very sensitive to micro and nano environment changes which make finding a material that mimics the embryonic stem cell niche properly a major challenge. During the past few years, many attempts have been made to build an appropriate artificial scaffold that mimics the stem cell niche and allows a better understanding and improvement of stem cell therapies. For instance, Webster and his colleagues had demonstrated the ability of carbon nanotubes in a polymer matrix to support orthopedic implants and neuronal cell growth and function. For example, when different cell types are cultured on carbon nanofibers reinforced polycarbonate urethane composite, they can result in an increase in neuronal cell numbers and the case of osteoblast cells further bone-forming. Despite the huge success of this system, the fate of carbon nanotubes remains unclear due to safety concerns that these materials still present in terms of toxicity, biocompatibility, and biodegradability.

Self-assembled peptide-based animal sources into nano fibrillar materials have been widely investigated recently for selective application such as differentiation and growth in both vitro and in vivo for a wide range of cells such as neural progenitor cells, primary bovine pulmonary artery endothelial cells, mouse osteoblastic cells and human mesenchymal cells.

For example, a nanofiber network of a self-assembling RAD16-I peptide scaffold developed by Elena Garreta and her colleagues proved to enhance the formation of an mES cell niche and enhance remarkably the frequency of Oct4 positive mES cell colonies compared to the ones cultured on the 2D system suggesting that the 3D-system culture condition enhanced the maintenance of cells with the embryonic phenotype in comparison with 2D scaffold.

The 3D biomaterials-based scaffold mentioned earlier seems to have great potential; unfortunately, problems related to the formation of such constructs in living organisms have not yet been investigated in-depth. Also, the immunogenicity of such constructs still constitutes a hurdle difficult to overcome.

Recently 3D scaffolds based on synthetic polymers gained a lot of intention mainly because of their biodegradability, biocompatibility, and flexibility in terms of functionalization with desired biomolecules. Also, polymeric materials can generate a more favorable microenvironment for stem cells development, by providing a complex network of nanofibers, gaps, and pores through which oxygen, hormones, and nutrients are delivered and waste products filtered away.

Nur-E-Kamal and his team reported the construction of a 3D nanofibrillar surface composed of polyamide nanofibers (Ultra-Web) that can promote the proliferation and self-renewal of mES cells. Moreover, the alkaline phosphatase staining of mES cell colonies revealed that stained colonies were significantly larger for mES cells cultured on Ultra-Web compared to the mES cells cultured on plain coverslips, which provides evidence that dimensionality plays an important role in maintaining stemness in proliferating mES cells.

Ouyang and coworkers showed the potential of poly (ethylene terephthalate) fibrous-based matrix to grow and maintain undifferentiated ES cells. The use of bioconjugate amphiphilic copolymers to generate 3D scaffolds for stem cell growth and differentiation is a fairly new concept when compared with what has been developed by other groups so far, especially in the field of stem cell biology and regenerative medicine.

Therefore, there is a need for a new synthetic 3D structure that overcomes the disadvantages of the existing 2D scaffolds by its ability to resemble more a living body than any other cell culture system, which means that the new synthetic structure can provide a more conducive microenvironment for stem cell culture (or tissue engineering) which eliminates animal by-products and their deleterious effects, normally occurring in traditional culture systems.

Herein we disclose the development of a new artificial 3D scaffold to support stem cell growth and later their differentiation, by converting biodegradable amphiphilic copolymers (star polymer) into nanowire scaffolds, through a molecular self-assembly process.

OBJECTS OF THE INVENTION

Objects of the present invention are to provide a method for producing artificial 3D scaffold to support stem cell growth and later their differentiation.

An object of the present invention is to provide a method for producing biodegradable artificial 3D nanowire scaffold to support stem cell growth and later their differentiation.

An object of the present invention is to provide a method for producing biodegradable amphiphilic copolymers (star polymer) to support stem cell growth and later their differentiation by converting biodegradable amphiphilic copolymers (star polymer) into nanowire scaffolds, through a molecular self-assembly process.

An object of the present invention is to provide a biodegradable artificial 3D nanowire scaffold to support stem cell growth and later their differentiation.

Another object of the present invention is to provide a method for growing and differentiating stem cells in the biodegradable artificial 3D nanowire scaffold without the loss of pluripotency.

Another object of the present invention is to provide a biodegradable artificial 3D nanowire scaffold comprising stem cells.

Yet another object of the present invention is to provide a biodegradable transplant/implant comprising the biodegradable artificial 3D nanowire scaffold.

SUMMARY OF THE INVENTION

This summary is provided to introduce a selection of concepts in a simplified form that are further described below in Detailed Description section. This summary is not intended to identify key features or essential features of the claimed subject matter, nor is it intended to be used as an aid in determining the scope of the claimed subject matter.

Aspects of the present disclosure pertains to a 3D scaffold for cell growth and proliferation. In particular, the present disclosure provides a method of producing an artificial 3D scaffold to support stem cell growth and later their differentiation, by converting biodegradable amphiphilic copolymers (star polymer) into nanowire scaffolds, through a molecular self-assembly process. The invention also relates to the use of said scaffold for cell culture and/or transplantation.

In an aspect, the present disclosure relates to a method for producing biodegradable artificial 3D nanowire scaffold (the poly(star)-Fibronectin nanowires) to support stem cell growth and later their differentiation.

In a preferred aspect, the present disclosure relates to a method for fabricating biodegradable copolymeric 3D nanowire scaffold to support cell growth and later their differentiation, said method comprises the steps of.

a. synthesizing polycaprolactone (PCL) macromonomer units;

b. synthesizing poly(ethylene glycol) (PEG) macromonomer units;

c. polymerizing the PCL macromonomer units and the PEG macromonomer units with a compound 1 having the structure:

Compound 1

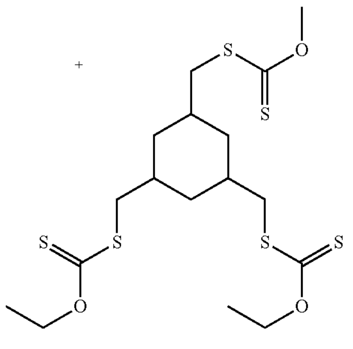

by Atom transfer radical polymerization (ATRP) polymerization to obtain an amphiphilic copolymer, poly(caprolactone)-b-poly(ethylene oxide) star-polymer having the structure:

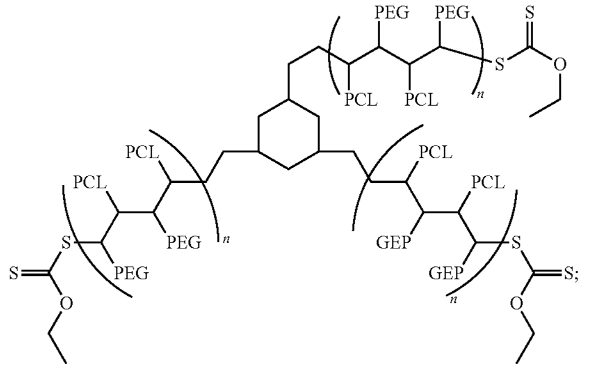

poly(caprolactone)-b-poly(ethylene-oxide) star-polymer d. providing PEG-fibronectin;

e. bioconjugation of poly(caprolactone)-b-poly(ethylene oxide) star-polymer with fibronectin by mixing poly (caprolactone)-b-poly(ethylene oxide) star-polymer with PEG-fibronectin in water soluble organic solvent, followed by stirring;

f. adding deionized water in frequent intervals, followed by dialysis against deionized water effecting the formation of biodegradable copolymeric 3D nanowire scaffold (poly(star)-Fibronectin nanowires) by a molecular self-assembly process, wherein, the molecular self-assembly process is effected by the solvent removal procedure, whereby slow removal of the organic phase triggers micellization that later leads to the formation of the nanowires; the concentration of the amphiphilic copolymer; and the molecular structure of the amphiphilic copolymer.

In one aspect, the present disclosure relates to a method for the synthesis of PCL macromonomer units effected by reacting PCL with triethylamine In one aspect, the present disclosure relates to a method for the synthesis of PEG macromonomer units effected by reacting PEG with triethylamine.

In one aspect, the present disclosure relates to a star-polymer having the structure:

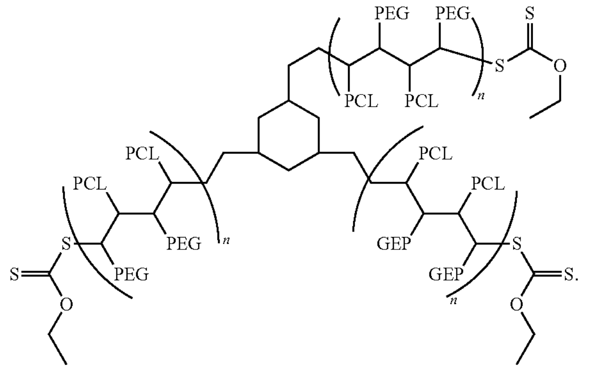

poly(caprolactone)-b-poly(ethylene-oxide) star-polymer

In another aspect, the present disclosure relates to a biodegradable copolymeric 3D nanowire scaffold (poly (star)-Fibronectin nanowires) to support cell growth and later their differentiation, wherein said scaffold is obtained by the method provided herein.

In another aspect, the present disclosure relates to a method of growing and differentiating pluripotent stem cell in the poly(star)-Fibronectin nanowires comprising the steps of: (i) seeding the pluripotent stem cells in the scaffold; and (ii) growing the pluripotent stem cells for a sufficient amount of time until differentiation or without the loss of pluripotency In yet another aspect, the present disclosure relates to a biodegradable copolymeric 3D nanowire scaffold comprising cultured pluripotent stem cells.

In yet another aspect, the present disclosure relates to a biodegradable transplant/implant comprising the poly(star)-Fibronectin nanowires.

Various objects, features, aspects and advantages of the inventive subject matter will become more apparent from the following detailed description of preferred embodiments.

BRIEF DESCRIPTION OF DRAWINGS

Characteristics and advantages of the subject matter as disclosed in the present disclosure will become clearer from the detailed description of an embodiment thereof, with reference to the attached drawing, given purely by way of an example, in which.

DETAILED DESCRIPTION OF THE INVENTION

Figure 1:
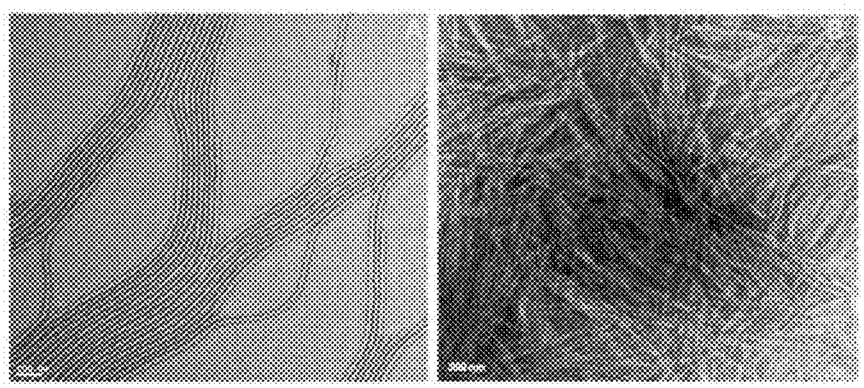
FIG. 1: Transmission Electron Microscope (TEM) by negatively staining with 1% uranyl acetate A) Individual nanowires. B) Network of nanowires forming a 3D scaffold.

The following is a detailed description of embodiments of the disclosure. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In some embodiments, numbers have been used for quantifying weight percentages, angles, and so forth, to describe and claim certain embodiments of the invention and are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Various terms as used herein are shown below. To the extent a term used in a claim is not defined below, it should be given the broadest definition persons in the pertinent art have given that term as reflected in printed publications and issued patents at the time of filing.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context requires otherwise, throughout the specification which follow, the word "comprise" and variations thereof, such as, "comprises" and "comprising" are to be construed in an open, inclusive sense that is as "including, but not limited to."

The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified.

The description that follows, and the embodiments described therein, is provided by way of illustration of an example, or examples, of particular embodiments of the principles and aspects of the present disclosure. These examples are provided for the purposes of explanation, and not of limitation, of those principles and of the disclosure.

The headings and abstract of the invention provided herein are for convenience only and do not interpret the scope or meaning of the embodiments.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Various terms are used herein. To the extent a term used in a claim is not defined below, it should be given the broadest definition persons in the pertinent art have given that term as reflected in printed publications and issued patents at the time of filing.

While a particular form of the invention has been illustrated and described, it will be apparent that various modifications can be made without departing from the spirit and scope of the invention.

The term “differentiate”, “differentiation”, “differentiated” or “differentiating” means any change in cellular gene expression accompanied by or accompanying the restriction of a cell and its progeny to a more specific cell-type lineage.

The term “Pluripotent,” or “pluripotency” refers to the ability of a single stem cell to give rise to all of the various cell types that make up the body of an animal.

The present disclosure pertains to a 3D scaffold for cell growth and proliferation. In particular, the present disclosure provides a method of producing an artificial 3D scaffold to support stem cell growth and later their differentiation, by converting biodegradable amphiphilic copolymers (star polymer) into nanowire scaffolds (poly(star)-nanowire), through a molecular self-assembly process. The invention also relates to the use of said scaffold for cell culture and/or transplantation.

In an embodiment, the present invention provides a method for fabricating biodegradable copolymeric 3D nanowire scaffold to support cell growth and later their differentiation, said method comprises the steps of:

a. synthesizing polycaprolactone (PCL) macromonomer units;
b. synthesizing poly(ethylene glycol) (PEG) macromonomer units;
c. polymerizing the PCL macromonomer units and the PEG macromonomer units with a compound 1 having the structure:

Compound 1

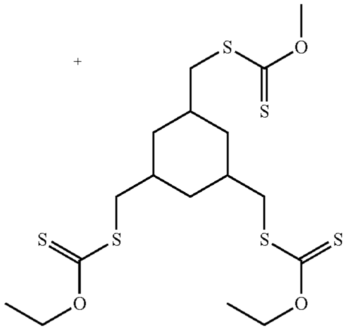

by Atom transfer radical polymerization (ATRP) polymerization to obtain an amphiphilic copolymer, poly(caprolactone)-b-poly(ethylene oxide) star-polymer;
d. providing PEG-fibronectin;
e. bioconjugation of poly(caprolactone)-b-poly(ethylene oxide) star-polymer with fibronectin by mixing poly (caprolactone)-b-poly(ethylene oxide) star-polymer with PEG-fibronectin in water soluble organic solvent, followed by stirring;
f. adding deionized water in frequent intervals, followed by dialysis against deionized water effecting the formation of biodegradable copolymeric 3D nanowire scaffold (poly(star)-Fibronectin nanowires) by a molecular self-assembly process.

In one embodiment of the present invention, the method comprises the step of synthesizing polycaprolactone (PCL) macromonomer units effected by reacting PCL with triethylamine.

In one embodiment of the present invention, the synthesis of PCL macromonomer units is effected by the following equation:

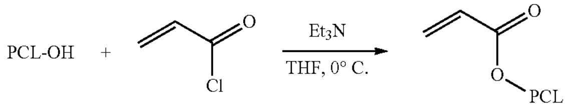

PCL macromonomer

In one embodiment of the present invention, the method comprises the step of synthesizing poly(ethylene glycol) (PEG) macromonomer units effected by reacting PEG with triethylamine.

In one embodiment of the present invention, the synthesis of PEG macromonomer units is effected by the following equation:

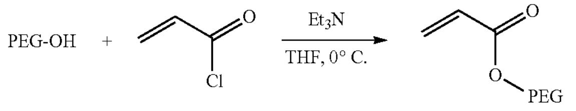

PEG macromonomer

In one embodiment of the present invention, the bioconjugation of PEG with fibronectin is performed by adding PEG-hydroxysuccinimide ester to a solution containing fibronectin in bicarbonate buffer, followed by gentle stirring for up to 5 days in slow tilt rotation at freezing temperatures.

In one embodiment of the present invention, the ATRP polymerization is effected in the ratio of PCL macromonomer units:PEG macromonomer units:Compound 1 by 1:1:1, respectively.

In one embodiment of the present invention, the ATRP polymerization is effected by Azo-bis-isobutyronitrile (AIBN) as the catalyst. It should be noted that the selection of catalyst is not limited to AIBN, and any catalyst that has similar functionality to AIBN can be employed as a catalyst for this reaction.

In one embodiment of the present invention, the ATRP polymerization is effected by the following equation:

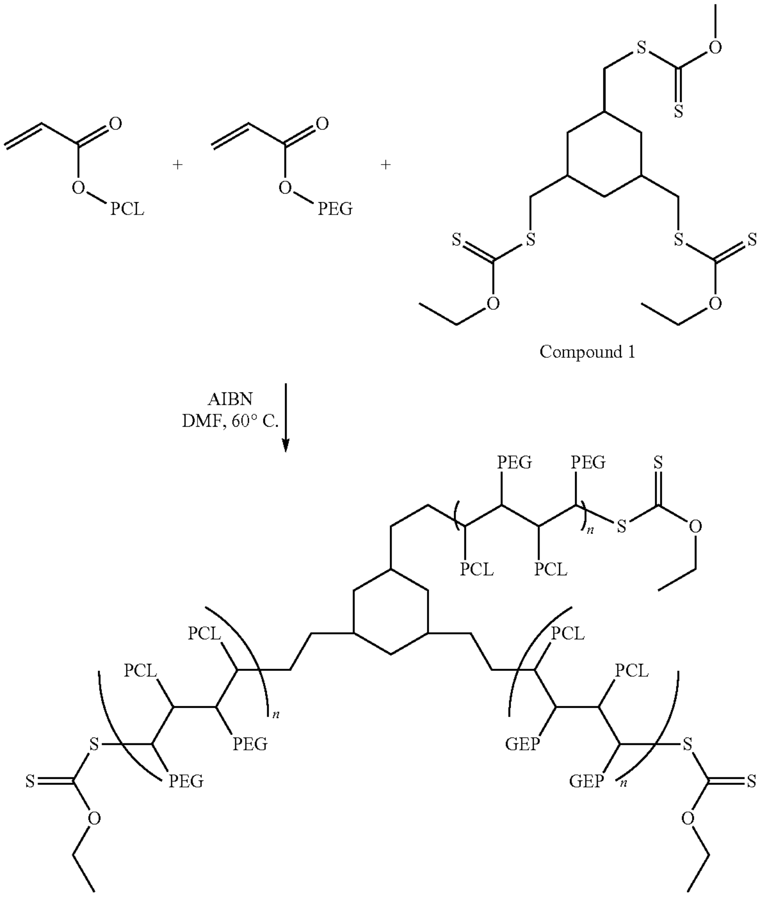

Compound 1 poly(caprolactone)-b-poly(ethylene oxide) star-polymer

In one embodiment of the present invention, the ATRP polymerization is effected by more than one time for desired yield. More preferably, twice.

In one embodiment of the present invention, the poly (caprolactone)-b-poly(ethylene oxide) star-polymer has a monomodal molecular weight distribution; te=23.07 min with an average Mn (GPC, PSSNa standards) around 14 kDa.

In one embodiment of the present invention, the ratio of amphiphilic copolymer to PEG-fibronectin is 3.3:1

In one embodiment, the present disclosure relates to a star-polymer having the structure:

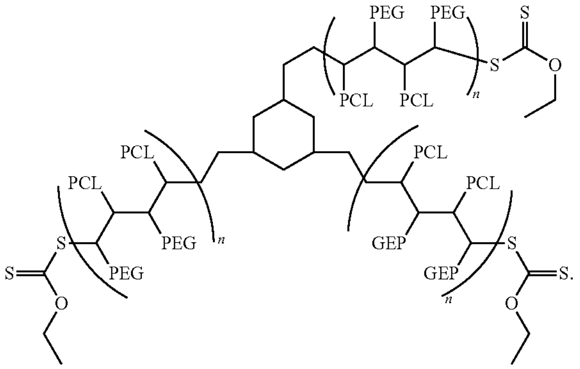

poly(caprolactone)-b-poly(ethylene-oxide) star-polymer

In one embodiment of the present invention, the water soluble organic solvent in step e) is selected from but not limited to methanol, ethanol, propanol, dimethylformamide (DMF), xylene, toluene, and the like. Preferably DMF.

In one embodiment of the present invention, the molecular self-assembly process is effected by the following parameters: (i) the solvent removal procedure, whereby slow removal of the organic phase triggers micellization that later leads to the formation of the nanowires; (ii) the concentration of the amphiphilic copolymer; and (iii) the molecular structure of the amphiphilic copolymer.

In one embodiment, the poly(star)-Fibronectin nanowires have an average length of from about 0.1 to about 10 μm. In one embodiment, the poly(star)-Fibronectin nanowires have an average length of from about 0.5 to about 5 μm. In another embodiment, the poly(star)-Fibronectin nanowires have an average length of from about 1 to about 2 μm. In one embodiment, 85 to about 96 percent of the nanowire scaffolds have length of from about 1 to about 2 μm.

In one embodiment, the poly(star)-Fibronectin nanowires have an average diameter of from about 1 to about 100 nm. In one embodiment, the poly(star)-Fibronectin nanowires have an average diameter of from about 10 to about 50 nm. In another embodiment, the poly(star)-Fibronectin nanowires have an average diameter of from about 20 to about 40 nm. In one embodiment, 85 to about 96 percent of the nanowire scaffolds have an average diameter of 30 nm.

In an embodiment, the present disclosure provides a biodegradable copolymeric 3D nanowire scaffold to support cell growth and later their differentiation, wherein said scaffold is obtained by the method disclosed herein.

In general, the poly(star)-Fibronectin nanowires for use with the invention provides a biocompatible substrate for stem cell growth, and differentiation for in vitro cell-based assays, implantation/transplantation of differentiated stem cells in an animal.

In one embodiment of the present invention, the cell is selected from a group consisting of stem cells, embryonic stem cells, pluripotent cells, multipotent cells, chondrocytes, osteoblasts, osteocytes, fibroblasts, bone marrow cells, stromal cells, chondrocyte progenitors, osteoclasts, endothelial cells, macrophages, adipocytes, monocytes, plasma cells, mast cells, umbilical cord cells, leukocytes, epithelial cells, myoblasts, and precursor cells derived from adipose tissue. Preferably stem cell. Most preferable pluripotent stem cell.

In one embodiment, when transplanted, the poly(star)-Fibronectin nanowires may further comprise one or more growth factors effective for stem cell proliferation and/or one or more therapeutic agents along with the seeded stem cells.

While the foregoing description discloses various embodiments of the disclosure, other and further embodiments of the invention may be devised without departing from the basic scope of the disclosure. The invention is not limited to the described embodiments, versions or examples, which are included to enable a person having ordinary skill in the art to make and use the invention when combined with information and knowledge available to the person having ordinary skill in the art.

EXAMPLES

The present disclosure is further explained in the form of following examples. However, it is to be understood that the foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

Reagents and Instruments

All reagents and solvents for synthesis were reagent grade and were used without further purification unless stated otherwise. Methacrylic acid (MAA) (Fluka) was distilled at low pressure in a Buchi Glass Oven B-585 micro distiller before use. Azobisisobutyronitrile (AIBN) (Fluka) was recrystallized from methanol and dried under a vacuum at room temperature. GRGDS (Sigma) was dissolved in Mili Q water to a concentration of 5 mg/mL. Polymer isolation and identification were performed as described in the reference. Azo-bis-isobutyronitrile (AIBN) was purchased from Fluka, crystallized from methanol, and dried under vacuum at room temperature. Anhydrous sodium sulphate and hydrochloric acid were purchased from Panreac. Methanol for GPC was Merck, HPLC grade. For dialysis and GPC Mili Q water was used. The dialysis cassettes were Pierce Biotech, 10 k MWCO.

Example 1: PCL Macromonomer Synthesis

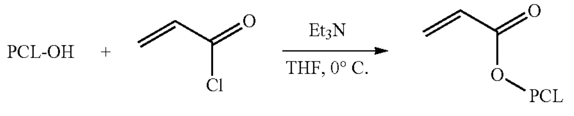

PCL macromonomer

Polycaprolactone PCL (average Mn ~530) (0.68 mmol) and triethylamine (1.36 mmol) were dissolved in 150 ml dried Tetrahydrofuran. Then acryloyl chloride (1.36 mmol) was added slowly to the mixture at 0° C. The reaction was kept at 0° C. for 5 hours, and then at 25° C. for 2 days. The polymer was then precipitated by addition of methanol and recovered via filtration process and dried overnight, under vacuum, at 40° C.

PEG Macromonomer Synthesis

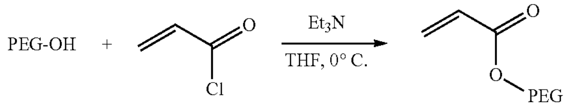

PEG macromonomer poly(ethylene oxide) PEG (average Mn ~1000) (0.68 mmol) and triethylamine (1.36 mmol) were dissolved in 150 ml dried Tetrahydrofuran. Then methyl acryloyl chloride (1.36 mmol) was added slowly to the mixture at 0° C. The reaction was kept at 0° C. for 5 hours, and then at 25° C. for 2 days. The polymer was then precipitated by addition of methanol and recovered via filtration process and dried overnight, under vacuum, at 40° C.

ATRP Polymerization

Compound 1 (45 equivalents) was dissolved in 10 mL of THF. And 45 equivalents of both PCL macromonomers, PEG macromonomer (1 equivalent) of AIBN were added to the solution. After the mixture was heated to 60° C., under stirring, for 4 days. The flask was then cooled down and 10 mL of Tetrahydrofuran was added to the mixture, The polymer was then separated from the supernatant by centrifugation at 15000 RPM for 30 min, followed by decantation.

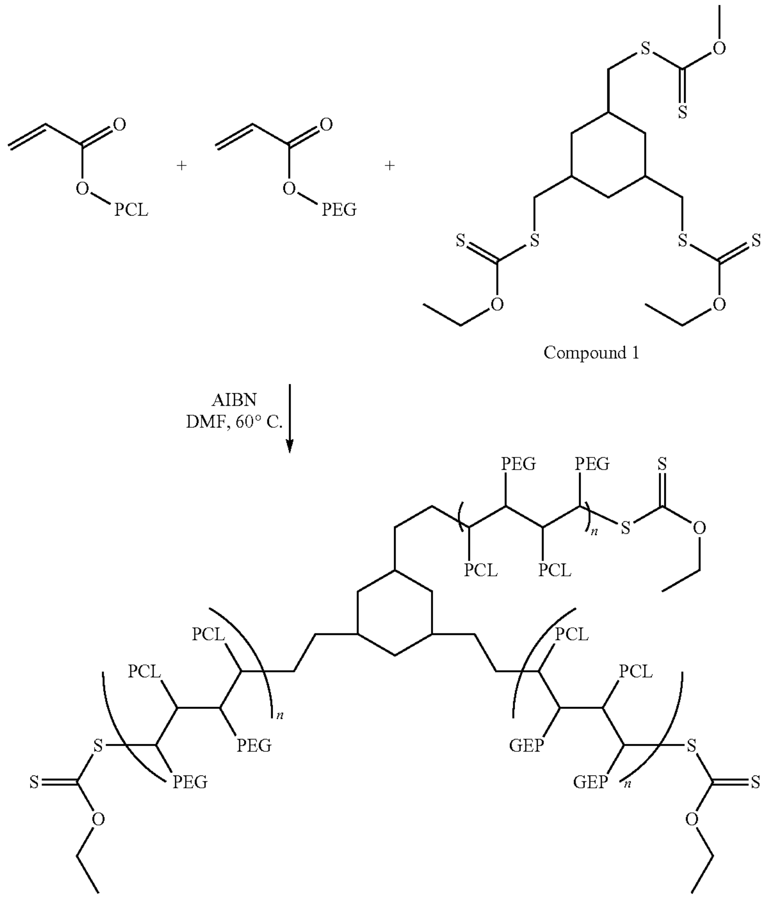

Compound 1 poly(caprolactone)-b-poly(ethylene oxide) star-polymer

This procedure was repeated twice to yield a white solid that was vacuum dried, at 30° C., for 24 h. 1H NMR (DMSO) 1.12 (s, CH3C—C═O), 1.2 (s, CH3C—C═O), 1.44 (t, CH3CH2O—C═S), 1.808 (s, CH2C—C═O), 2.1 (s, CH2C—C═O), 3.45 (s, CH3O—(CH2CH2O)n), 3.7 (s, (CH2CH2O)n), 4.56 (q, CH3CH2O—C═S). GPC analysis (PSSNa standards) reveals a monomodal molecular weight distribution; te=23.07 min with an average Mn (GPC, PSSNa standards) around 14 kDa, which has been confirmed with MALDI.

Bioconjugation with Fibronectin

Bioconjugation of PEG with fibronectin was performed as follows: 40 mg of PEG-hydroxysuccinimide ester was added to a solution containing 10 μg of fibronectin in 0.1 M bicarbonate buffer (500 μL, pH=8.3). The mixture was gently stirred for 5 days in slow tilt rotation at 4° C.

Polymeric Nanowires Formation

The assembly of co-polymer into nanowire was achieved as follows: poly(caprolactone)-b-poly(ethylene oxide) star-polymer 100 mg with 30 mg PEG-fibronectin were dissolved in DMF, the solution was then stirred for 3 h. Deionized water will be added at a rate of 10 μl every 5 s for a total of 1.6 ml to induce the nanowire formation. The aqueous solution was then dialyzed against deionized water for days 4. Throughout the last step, the synthetic amphiphilic copolymer undergoes self-assembly into well-ordered and homogenous soft nanowires often 1-2 μm long and 30 nm diameter as characterized by TEM.

The assembly of these co-polymers into nanofiber was achieved as follows: poly(caprolactone)-b-poly(ethylene oxide) star-polymer (40 mg) were dissolved in DMF, the solution was then stirred for 3 h. Deionized water was added at a rate of 10 μl every 5 s for a total of 1.6 ml to induce the nanowire formation. The aqueous solution was then dialyzed against deionized water for 4 days. Throughout the last step the synthetic amphiphilic copolymer, undergo self-assembly into well-ordered and homogenous soft nanowires often 1-2 μm long and 30 nm diameter (FIG. 1A), at high concentration these nanowires tend to be predisposed to form 3D scaffold with tiny gaps and pores (FIG. 1B), through which oxygen, hormones, and nutrients can be delivered and waste products to be filtered away to increase in vivo like characteristic of these artificial structures.

Figure 2:
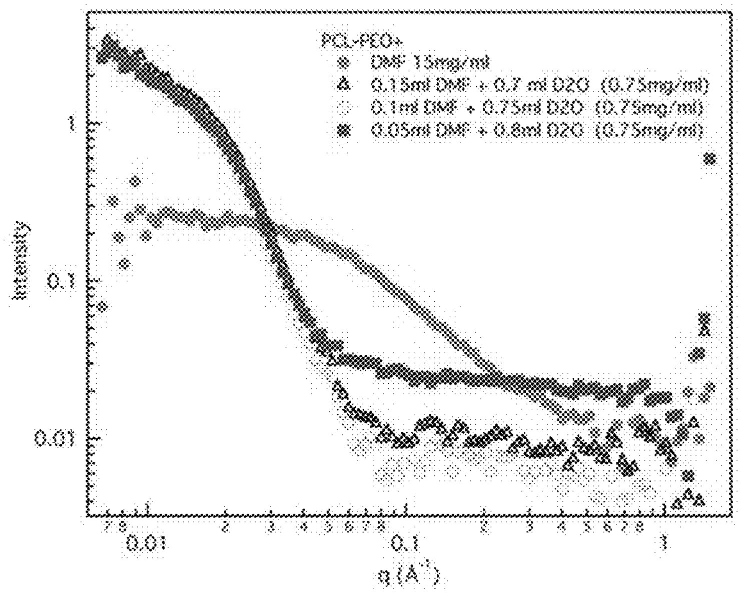
FIG. 2: Small-angle neutron diffraction (SAND) Neutron Diffraction plots of block copolymer in D2O at different concentrations of organic solvent/D2O.

To identify the mechanism by which these nanowires are fashioned, a series of experiments was conducted using Transmission Electron Microscope (TEM) and Small Single Neutron Diffraction technique and the data collected from these analyses suggest that the building mechanism of the nanofiber assembly depends on three factors: first the solvent-removal procedure. For water-miscible organic solvents, the copolymer mixture can be dialyzed against water, whereby slow removal of the organic phase triggers micellization that later leads to the formation of the nanowires. By using SASI (small-angle scattering instrument) to determent the small-angle neutron diffraction analysis, we can observe the dependence of the nanowire formation on the solvent-removal procedure, where the cylindrical shapes were observed at a lower percent of the organic solvent compared with water (FIG. 2).

Figure 3:
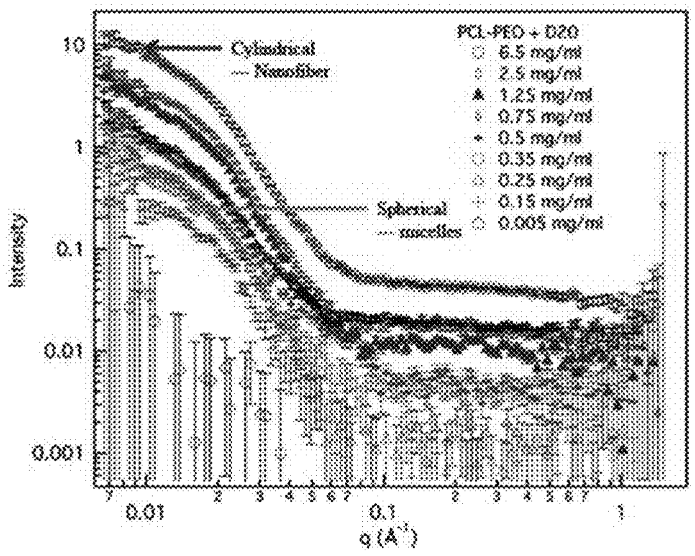
FIG. 3: SAND scattered intensity profiles of block copolymer in D2O at different concentrations of polymer.

The impact of the polymer concentration was evaluated by small-angle neutron diffraction (SAND). A series of samples with different copolymer concentrations were prepared. As depicted in FIG. 3, the Neutron Diffraction plots show clear evidence that the transition from spherical micelles to elongated nanofiber structures depends heavily on the concentrations of the polymer in solution; the higher the concentration the faster the nanofiber formation.

Figure 4:
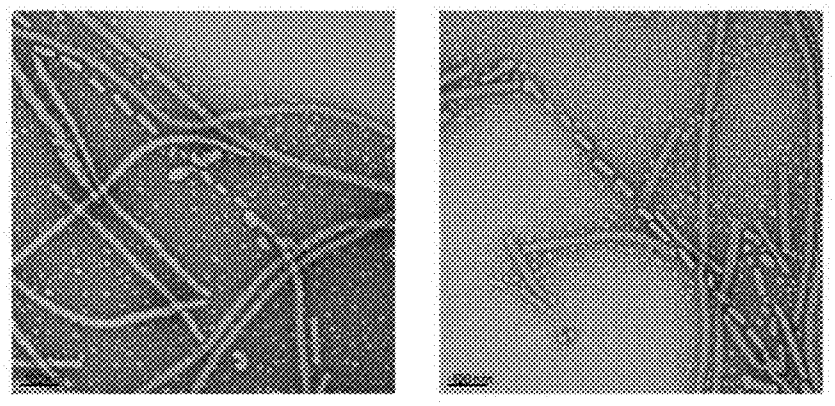
FIG. 4: Fusions process or micelle stacking that leads to the elongation of the cylindrical shaped micelle into nanofibers.

Also, the transition of the copolymer macro-molecules from spherical shapes to elongated nanofibers were probed by Transmission Electron Microscope (TEM) and the images show clearly, that samples with low concentration (0.1-0.20 mg/ml of the copolymer) do not contain any nanowire structures, except for polymeric micelles that appears to be the predominate geometrical form in these samples, however under certain condition such as long time storage, we observed the formation of some nanowire and that is probably due to the reduction of the initial volume of the samples as a result of the evaporation factor, or to a very slow micelles pileup process. However, when the concentration reaches 0.7 mg/ml, we started to observe the formation of cylindrical-shaped micelles. Furthermore, as the concentration increase to 1 mg/ml, inter-micelle interactions prompt a series of fusions between micelles (micelle stacking) that leads to the elongation of the cylindrical shaped micelle into nanofibers (FIG. 4) and nanofibers become the dominant structures in the solution. It is also interesting to note that once the fibers are formed, they are stable in water even if overall polymer concentrations are below the critical fiber concentration which is 0.7 mg/ml. The last factor that we believe has a big impact on the size and the shape of this nanowire is the molecular structure of the amphiphilic copolymer. It is well-known that the self-assembly of the amphiphilic copolymer into nanowires depends mainly on the weight fraction w of the hydrophilic block relative to the total copolymer molecular weight. For poly(ethylene oxide) (PEO)-based diblock in aqueous solution, where $w_{EO}$~45-55% leads to the assembly of main nanowires but higher w gives predominantly spherical micelles, and lower w yields vesicles.

Figure 5:
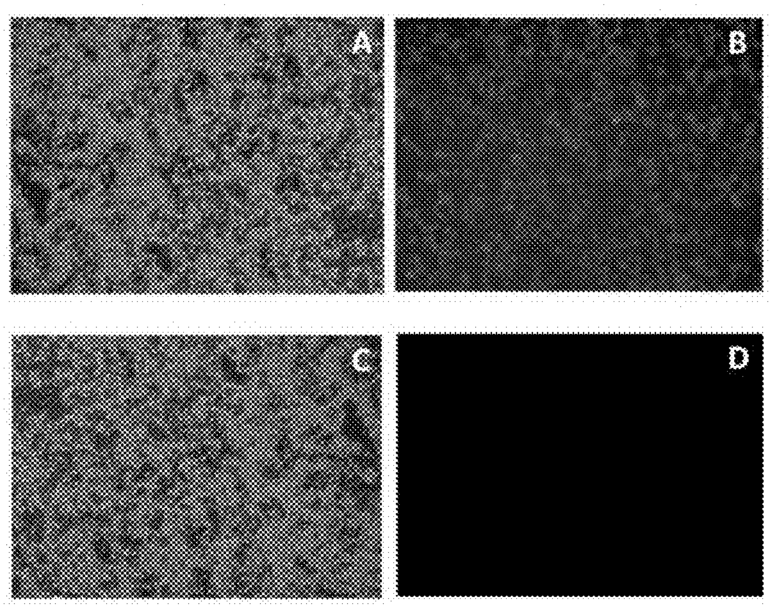
FIG. 5: Fluorescence imaging A) Light optical microscope image of the bioconjugation of the nanowires with fibronectin. B) fluorescence microscopy images of the bioconjugation of the nanowires with fibronectin. C) Light optical microscope image of the pure nanowires without the fibronectin. D) fluorescence microscopy images of the pure nanowires without the fibronectin.

The first step toward the fabrication of this artificial scaffold is the synthesis of bioconjugated nanowires with fibronectin. Fibronectin is a cell-surface and serum-derived glycoprotein and has numerous effects on cells in vitro. At concentrations as low as 1-50 ug/ml, it can promote the adhesion, spreading, migration of fibroblasts and certain other cells, and induce transformed cells to flatten and appear normal. Additionally, fibronectin can influence the differentiation of chondrocytes and myoblasts. The preparation of bioconjugated nanowires with human fibronectin was carried out by conjugating PEG 20000 with the fibronectin to form PEG-fibronectin, followed by mixing PEG-fibronectin with the amphiphilic copolymer start with a ratio of 1 to 3.3. The resulting solution was then placed in a dialysis cassette and dialyzed against deionized water for 4 days at 4° C. to yield a fibronectin conjugated nanowire. To confirm the presence of fibronectin on the surface of the nanowires, fibronectin conjugated nanowires were first deposited on the surface of the petri dish, then a solution of amine-reactive fluorescent dye (Alexa Fluor® 488 carboxylic acid, succinimidyl ester) was added to the petri dish and left for 4 hours, to allow the tethering reaction between the dye and the proteins to occur. After several washing, images of Fibronectin conjugated nanowires were taken by fluorescence microscope. A control experiment was performed using block co-polymer nanowires without Fibronectin using the same procedure. As depicted in FIG. 5, the fluorescence observed in FIG. 5B confirms the bioconjugation of the nanowires with fibronectin. This fluorescence is indicative in contrast to its control showed no florescence activity was observed in the case of pure nanowires (FIG. 5C).

Example 2: Cell Cultivation

Mouse embryonic stem cells (mESCs) were seeded in 3 wells of a 6-well plate at 50000 cells/well with poly(star)-Fibronectin nanowires and left for 24 and 48 hours in culture. The cells were removed from the poly(star)-Fibronectin nanowires by washing the nanowires with a medium. For control experiments, cells were seeded in Embryonic Fibroblasts (MEFs) in 3 wells of a 6-well plate at 50000 cells/well. The total number of cells and the viability of the cells were determined using propidium iodide incubation.

Figure 6:
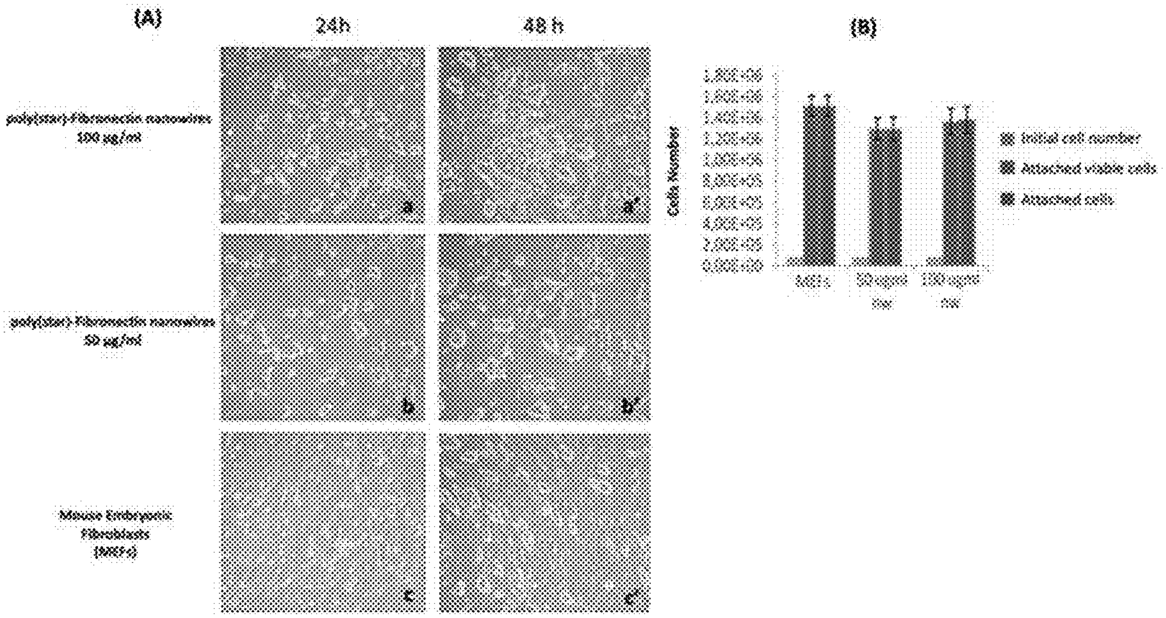
FIG. 6: Cell proliferation. (A) mouse embryonic stem cells (mESCs) growth and proliferation over 24 and 48 hours in different culture media during; (a, a': poly(star)-Fibronectin nanowires 100 μg/ml. b, b': poly(star)-Fibronectin nanowires 50 μg/ml. c, c': Mouse Embryonic Fibroblasts cells) magnification=×100. (B) the illustrated data of viability test value of three independent experiments ±S.D (cell number difference between nanowires compared to the negative reference value (TCPS) ($p<0.001$).

To assess the poly(star)-Fibronectin nanowires to sustain mouse embryonic stem cells (mESCs) cultures, we investigated the poly(star)-Fibronectin nanowire's ability to support mES cells adhesion and growth. Undifferentiated mES cells were cultured for 2 and 3 days on various concentrations of poly(star)-Fibronectin nanowires and compared to cells cultures in mouse embryonic fibroblasts (MEFs), gelatin, and standard polystyrene as a control experiment. The morphology, viability, and proliferation of these cells were investigated. After 3 days of incubation on nanowires, the microscope visualization showed the appearance of a new colony with clear and defined borders, tightly-packed and dome-shaped similar to these colonies obtained with MEFs (FIG. 6), which represent a good indication that these cells kept their pluripotency feature. In addition, the obtained results concern the mES cells' proliferation on the nanowires for 48 hours were similar to commercials culture media such as MEFs. This appears to indicate that the nanowires could be used as an alternative to commercial culture media supporting mES cell growth.

Example 3: Proliferation and Viability Assays

The ability of the poly(star)-Fibronectin nanowires to support mES cells in an undifferentiated state will be tested by evaluating the growth and viability of these cells along with their morphology. In this study, undifferentiated Mouse embryonic stem cells (mESCs) (50000 cells/well) were seeded on 100, 50 μg/ml poly(star)-Fibronectin nanowires, and on Mouse Embryonic Fibroblasts (MEFs) in a standard TCPS six-well plate for 2 and 3 days. Flow cytometry was utilized to determine the total number of cells and the viability of the cells was determined using propidium iodide incubation.

For the flow cytometry, the culture medium was removed, and then the cells were washed and trypsinized. The cells were collected in a polystyrene tube and then incubated with propidium iodide (5 μg/ml) before analysis by modular, benchtop flow cytometer from Becton Dickinson Immunocytometry System (BDIS). The viability is the ratio between the number of viable cells and the total number of cells. Cell proliferation was determined as the ratio between viable cells and initial cell number.

Example 4: Alkaline Phosphatase Assay

The pluripotency of mouse embryonic stem cells (mESCs) was determined by alkaline phosphatase (ALP)

staining performed on day 3 of culture, using an Alkaline Phosphatase Live Stain (Thermo Fischer Scientist) in accordance with the manufacturer's manual. In brief, the cells were fixed with citrate/acetone/formaldehyde solution for 4 minutes, and then washed twice with Milli-Q water, then cells are stained with Alkaline Phosphatase Staining solution for 30 min and counterstained with haematoxylin for 4 minutes. The morphology of the colonies and ALP-positive cells were assessed with an inverted light microscope.

Figure 7:
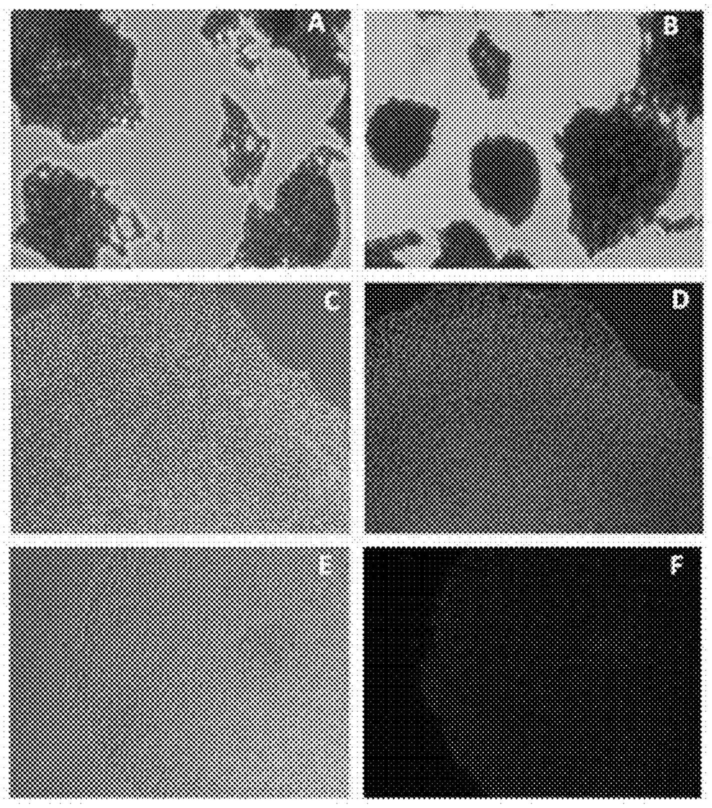
FIG. 7: (A and B) Images of mouse embryonic stem cells (mESCs) that have been stained with ALP after 48 hours (magnification=×100). (C and D) Oct4 marker staining of cells grown on poly(star)-Fibronectin nanowires. (E and F) SSEA4 marker staining of cells grown on poly(star)-Fibronectin nanowires.

Determination of the long-term impact of poly(star)-Fibronectin nanowires on mES cells in terms of pluripotency, an alkaline phosphatase test was carried out using cultured mES cells in 100, 50 μg/ml of poly(star)-Fibronectin nanowires and in control conditions. Alkaline phosphatase staining indicted that alkaline phosphatase activity was present in all mES cells cultured on poly(star)-Fibronectin nanowires independently of the time of culture (2 or 3 days). In fact, mES cells cultured on poly(star)-Fibronectin nanowires resemble more the colonies that form when mES cells are cultured on a monolayer of fibroblasts where all cells are alkaline phosphatase positive and colonies are dome-shaped (FIG. 7). These results suggest that nanofibers may be used as an alternative to conventional gelatin to support the growth of undifferentiated ES cell cultures.

Further, Quantitative RT-PCR for stem cell markers (Oct4 and SSEA4) was carried out using RNA extracted from mES cells that have been cultured on 100 and 50 μg/ml of poly(star)-Fibronectin nanowires. The data obtained showed that the expression levels of Oct4 were in the order of 1.37 and 1.24-fold higher compared to mES cells that have been seeded in MEFs. Furthermore, the expression level of both markers Nanog and SSEA4 were similar to those that have been seeded in MEFs. In conclusion, these results suggest that the polymeric scaffolds not only support stem cells' growth and proliferation but also preserve the mES cell pluripotency.

Various modification and variation of the described assays, techniques and various means disclosed herein to implement the assays/methods in accordance with the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

1. Kanani, G. A. & Bahrami, H. S. Review on electrospun nanofibers scaffold and biomedical applications. *Trends Biomater. Artif. Organs* 24, 93-115 (2010).
2. Gösta Gahrton & Bo Björkstrand. Allogeneic transplantation in multiple myeloma. *Haematologica* 93, 1295-1300 (2008).
3. Strauer, B. E., Schannwell, C. M. & Brehm, M. Therapeutic potentials of stem cells in cardiac diseases. *Minerva Cardioangiologica* vol. 57 249-267 (2009).
4. Webster, T. J., Waid, M. C., Mckenzie, J. L., Price, R. L. & Ejiofor, J. U. Nano-biotechnology: Carbon nanofibres as improved neural and orthopaedic implants. *Nanotechnology* 15, 48-54 (2004).
5. Yang, L., Zhang, L. & Webster, T. J. Carbon nanostructures for orthopedic medical applications. *Nanomedicine* 6, 1231-1244 (2011).
6. Silva, G. A. et al. Selective Differentiation of Neural Progenitor Cells by High-Epitope Density Nanofibers. *Science* (80-.). 303, 1352-1355 (2004).
7. Tysseling-Mattiace, V. M. et al. Self-Assembling Nanofibers Inhibit Glial Scar Formation and Promote Axon Elongation after Spinal Cord Injury. *J. Neurosci.* 28, 3814-3823 (2008).
8. Sargeant, T. D., Rao, M. S., Koh, C.-Y. & Stupp, S. I. Covalent functionalization of NiTi surfaces with bioactive peptide amphiphile nanofibers. *Biomaterials* 29, 1085-1098 (2008).
9. Horii, A., Wang, X., Gelain, F. & Zhang, S. Biological Designer Self-Assembling Peptide Nanofiber Scaffolds Significantly Enhance Osteoblast Proliferation, Differentiation and 3-D Migration. *PLoS One* 2, e190 (2007).
10. Tambralli, A. et al. A hybrid biomimetic scaffold composed of electrospun polycaprolactone nanofibers and self-assembled peptide amphiphile nanofibers. *Biofabrication* 1, 025001 (2009).
11. Garreta, E., Genové, E., Borrós, S. & Semino, C. E. Osteogenic Differentiation of Mouse Embryonic Stem Cells and Mouse Embryonic Fibroblasts in a Three-Dimensional Self-Assembling Peptide Scaffold. *Tissue Eng.* 12, 2215-2227 (2006).
12. Fouzi, M., Thimma, M., BinSabt, M., Husain, A. A. & Aouabdi, S. Stem cell growth and proliferation on RGD bio-conjugated cotton fibers. *Biomed. Mater. Eng.* 32, 39-52 (2021).
13. Nur-E-Kamal, A., Ahmed, I., Kamal, J., Schindler, M. & Meiners, S. Three-Dimensional Nanofibrillar Surfaces Promote Self-Renewal in Mouse Embryonic Stem Cells. *Stem Cells* 24, 426-433 (2006).
14. Ouyang, A., Ng, R. & Yang, S.-T. Long-Term Culturing of Undifferentiated Embryonic Stem Cells in Conditioned Media and Three-Dimensional Fibrous Matrices Without Extracellular Matrix Coating. *Stem Cells* 25, 447-454 (2007).
15. Geng, Y., Ahmed, F., Bhasin, N. & Discher, D. E. Visualizing Worm Micelle Dynamics and Phase Transitions of a Charged Diblock Copolymer in Water. *J. Phys. Chem. B* 109, 3772-3779 (2005).

The invention claimed is:

1. A method for fabricating biodegradable copolymeric 3D nanowire scaffold to support cell growth and later their differentiation, said method comprises the steps of:

a. synthesizing polycaprolactone (PCL) macromonomer units;

b. synthesizing poly(ethylene glycol) (PEG) macromonomer units;

c. polymerizing the PCL macromonomer units and the PEG macromonomer units with a compound 1 having the structure:

Compound 1

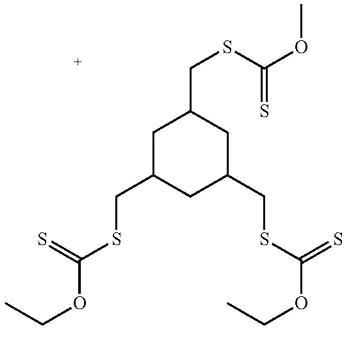

by Atom transfer radical polymerization (ATRP) polymerization to obtain an amphiphilic copolymer, poly(caprolactone)-b-poly(ethylene oxide) star-polymer;

d. providing PEG-fibronectin;

e. bioconjugation of poly(caprolactone)-b-poly(ethylene oxide) star-polymer with fibronectin by mixing poly (caprolactone)-b-poly(ethylene oxide) star-polymer with PEG-fibronectin in DMF, followed by stirring;

f. adding deionized water in frequent intervals, followed by dialysis against deionized water effecting the formation of biodegradable copolymeric 3D nanowire scaffold (poly(star)-Fibronectin nanowires) by a molecular self-assembly process, wherein, the molecular self-assembly process is effected by the solvent removal procedure by dialysis, whereby slow removal of the organic phase triggers micellization that later leads to the formation of the nanowires; the concentration of the amphiphilic copolymer; and the molecular structure of the amphiphilic copolymer.

2. The method according to claim 1, wherein the synthesis of PCL macromonomer units is effected by reacting PCL with triethylamine.

3. The method according to claim 1, wherein the synthesis of PEG macromonomer units is effected by reacting PEG with triethylamine.

4. The method according to claim 2 or 3, wherein the synthesis of PCL macromonomer units and PEG with triethylamine is effected by Tetrahydrofuran and methyl acryloyl chloride/acryloyl chloride as the catalysts.

5. The method according to claim 1, wherein the ATRP polymerization uses Azo-bis-isobutyronitrile (AIBN) as the catalyst.

6. The method according to claim 1, wherein the ratio of PCL macromonomer units: PEG macromonomer units: Compound 1 is 1:1:1.

7. The method according to claim 1, wherein the poly (caprolactone)-b-poly(ethylene oxide) star-polymer is mixed with PEG-fibronectin in the ratio of 3.3:1.

8. The method according to claim 1, wherein the amphiphilic copolymer, poly(caprolactone)-b-poly(ethylene oxide) star-polymer has the structure:

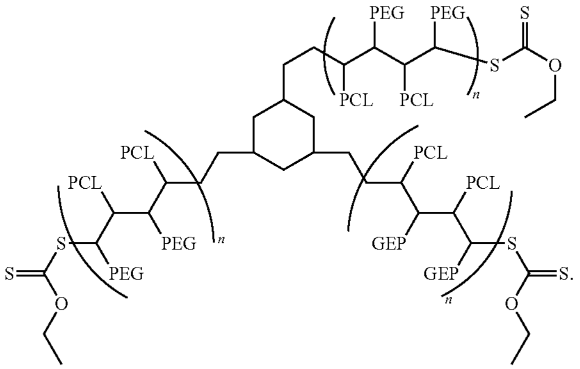

poly(caprolactone)-b-poly(ethylene-oxide) star-polymer

* * * * *